United States Patent [19]
Baker

[11] Patent Number: 5,658,305
[45] Date of Patent: Aug. 19, 1997

[54] SURGICAL ROUTER BIT

[76] Inventor: John W. Baker, 4 Wachusett Dr., Acton, Mass. 01720

[21] Appl. No.: 490,108

[22] Filed: Jun. 7, 1995

Related U.S. Application Data

[63] Continuation of Ser. No. 368,737, Jan. 4, 1995, abandoned, which is a continuation of Ser. No. 980,423, Nov. 23, 1992, abandoned, which is a continuation of Ser. No. 895,575, Jun. 8, 1992, abandoned, which is a continuation of Ser. No. 575,964, Aug. 31, 1990, abandoned.

[51] Int. Cl.$^6$ .................................................. A61B 17/16
[52] U.S. Cl. .......................... 606/180; 606/80; 408/224; 408/230
[58] Field of Search .................. 606/80, 180; 433/165; 408/229, 230, 224, 225

[56] References Cited

U.S. PATENT DOCUMENTS

| | | | |
|---|---|---|---|
| 1,358,432 | 11/1920 | Fink | 433/165 |
| 2,974,965 | 3/1961 | Welles | 408/229 X |
| 4,189,266 | 2/1980 | Koslow | 408/230 X |
| 4,475,850 | 10/1984 | Penoza et al. | 408/229 X |
| 4,537,185 | 8/1985 | Stednitz | |

FOREIGN PATENT DOCUMENTS

| | | | |
|---|---|---|---|
| 361315 | 11/1931 | United Kingdom | 433/165 |

*Primary Examiner*—Michael H. Thaler
*Attorney, Agent, or Firm*—Pandiscio & Pandiscio

[57] ABSTRACT

A novel surgical router bit is disclosed which comprises a shaft having a distal end and a proximal end and an outer surface tapering outwardly from its distal end to its proximal end, at least one spiral cutting flute or groove formed in and extending along the length of the shaft from the distal end of the shaft to the proximal end of the shaft, with the at least one spiral cutting flute or groove having a planar floor which is inclined relative to the center axis of the router bit, wherein for each pitch of the at least one spiral cutting flute or groove, the distal end of the floor is level with the tapering outer surface of the shaft and the proximal end of the floor has a fixed depth relative to the tapering outer surface of the shaft so as to define a helical cutting edge of fixed height, and at least one straight cutting flute or groove formed in and extending along the length of the shaft from the distal end of the shaft to the proximal end of the shaft, the at least one straight cutting flute or groove having a fixed depth relative to the tapering outer surface of the shaft so as to define a straight cutting edge of fixed height, and the at least one straight cutting flute or groove being superimposed on and intersecting the at least one spiral cutting flute. Preferably the surgical router bit comprises a plurality of spiral cutting flutes or grooves arcuately spaced apart around the circumference of the shaft, and a plurality of straight cutting flutes or grooves arcuately spaced apart around the circumference of the shaft.

2 Claims, 5 Drawing Sheets

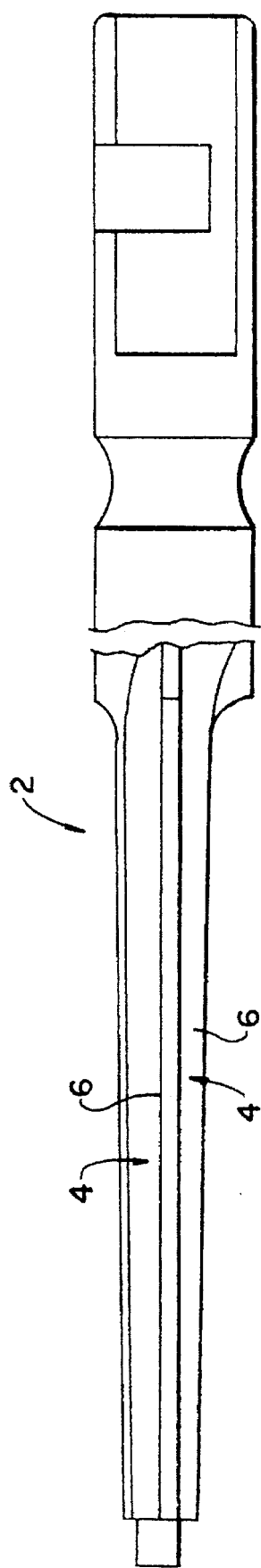
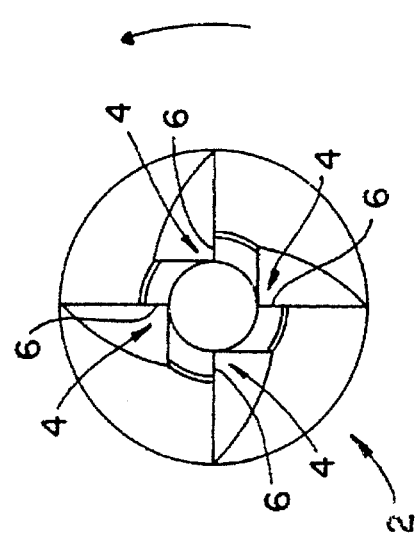
Fig. 1
PRIOR ART
Fig. 2
PRIOR ART

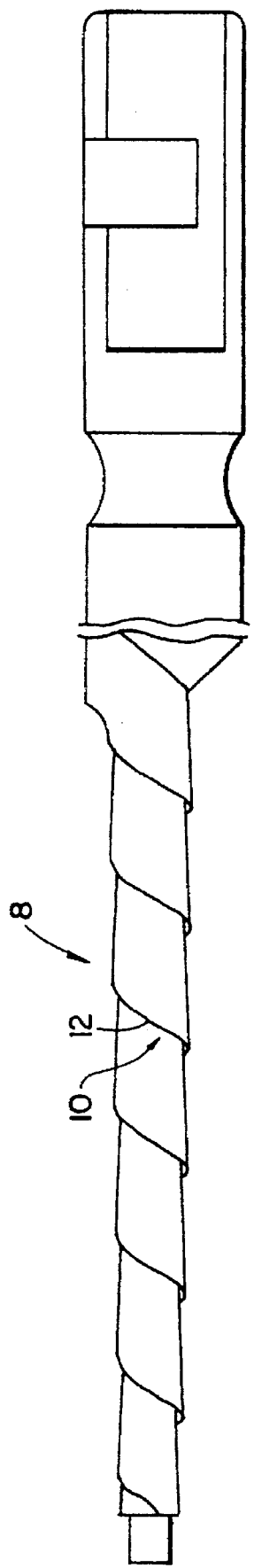
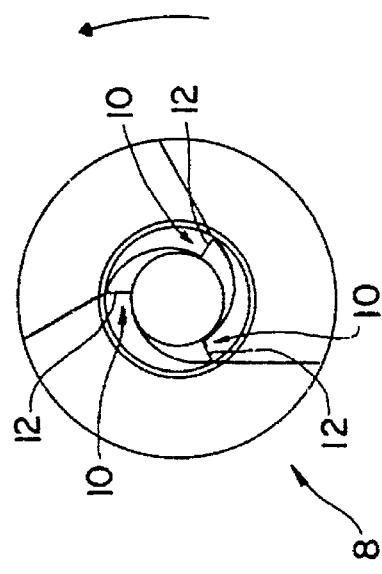
Fig. 3
PRIOR ART
Fig. 4
PRIOR ART

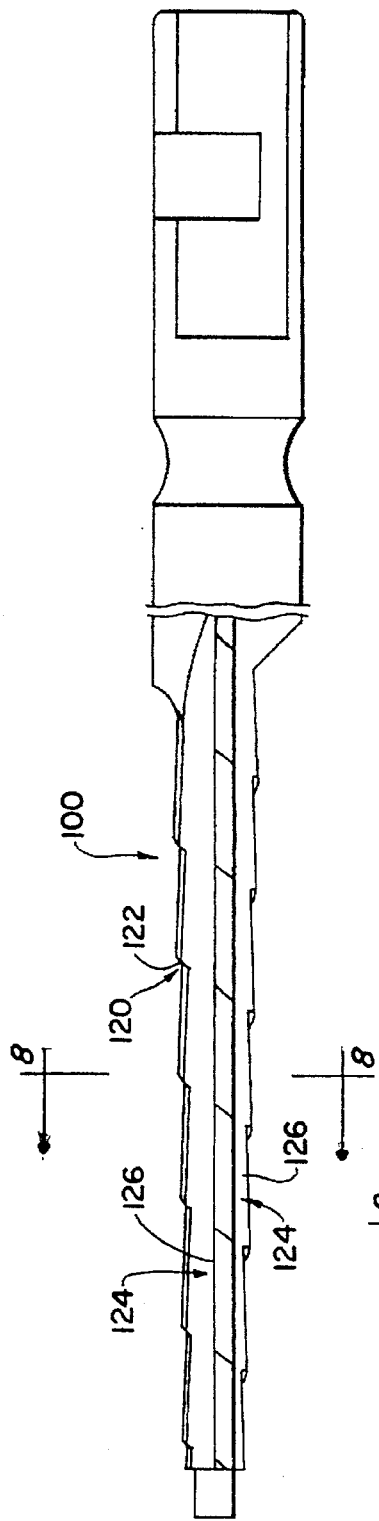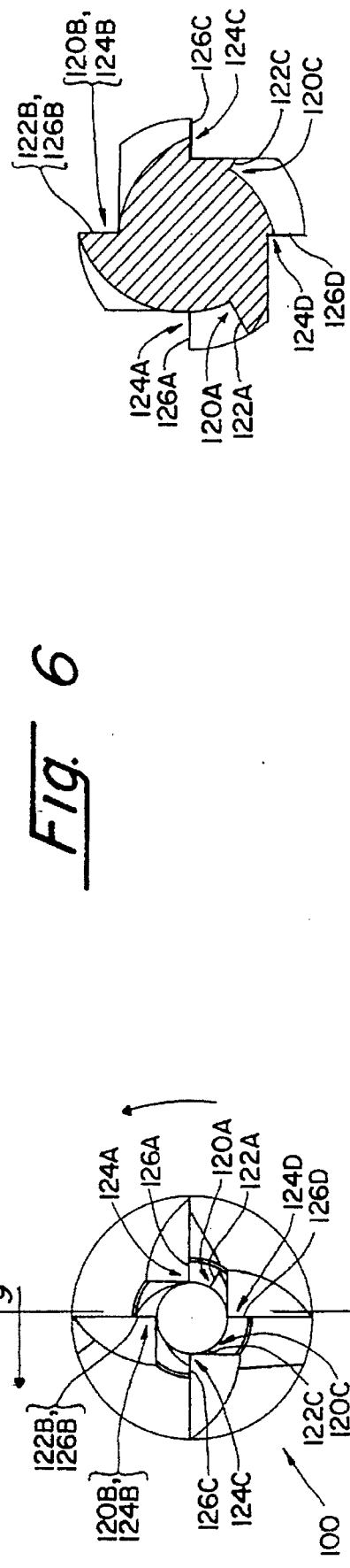

SURGICAL ROUTER BIT

This is a continuation of copending application Ser. No. 08/368,737 filed on Jan. 4, 1995, Which was in turn a continuation of prior U.S. patent continuation application Ser. No. 07/980,423 filed on Nov. 23, 1992, which was in turn a continuation of prior U.S. patent application Ser. No. 07/895,575 filed on Jun. 8, 1992, which was in turn a continuation of prior U.S. patent application Ser. No. 07/575,964 filed on Aug. 31, 1990 all of which are now abandoned.

FIELD OF THE INVENTION

This invention relates to router bits in general, and more particularly to surgical router bits of the sort adapted to cut human or animal bones.

BACKGROUND OF THE INVENTION

Surgical router bits are used in certain surgical procedures to cut human or animal bones.

Conventional surgical router bits generally utilize either straight or spiral cutting flutes or grooves.

More particularly, and looking now at FIGS. 1 and 2, there is shown a conventional surgical router bit 2 of the sort having a plurality of straight cutting flutes or grooves 4. Typically four straight cutting flutes 4 are provided, although more or less than that number may be used. For the sake of example, four straight cutting flutes 4 are provided on the router bit shown in FIGS. 1 and 2. Each of the cutting flutes 4 defines a straight cutting edge 6 which, when the router bit is engaged with bone and the router bit is rotated in a counterclockwise direction (as seen from the angle of view of FIG. 2), will cut through the bone.

Looking next at FIGS. 3 and 4, there is shown a conventional surgical router bit 8 of the sort having a plurality of spiral cutting flutes or grooves 10. Typically two, three or four spiral cutting flutes 10 are provided, although more or less than that number may be used. For the sake of example, three spiral cutting flutes 10 are provided on the router bit 8 shown in FIGS. 3 and 4. Each of the cutting flutes 10 comprises a right hand cut, left hand spiral geometry defining a helical cutting edge 12 which, when the router bit is engaged with bone and the router bit is rotated in a counterclockwise direction (as seen from the angle of view of FIG. 4), will cut through the bone.

Conventional surgical router bits of the sort described above typically suffer from a number of disadvantages.

For one thing, such conventional surgical router bits tend to clog with bone debris as they cut through the bone.

For another thing, such conventional surgical router bits tend to subject the router bit to significant loads during cutting, with the result that the router bit can break or the bone can be damaged during cutting.

Furthermore, it has been found that with at least some prior art surgical router bits, the surgical router bit must be driven at the relatively high speed of 65,000 rpm in order to obtain acceptable cutting results. However, the use of such high rpm driving speeds is not preferred, inasmuch as almost all of the power units currently available in the field are adapted to run only at the relatively slow speed of 20,000 rpm. In addition, since the use of such high driving speeds can result in substantial heat being generated during cutting by virtue of the engagement of the router bit with the surrounding bone, and since this heat can actually burn the bone if the router bit should clog while the router bit is being driven at these higher speeds, the use of such high driving speeds is not preferred.

OBJECTS OF THE INVENTION

As a result, the principal object of the present invention is to provide an improved surgical router bit which avoids the problems associated with prior art surgical router bits.

Another object of the present invention is to provide an improved surgical router bit which minimizes clogging of the router bit with bone debris during cutting.

Still another object of the present invention is to provide an improved surgical router bit which minimizes the load on the router bit during cutting, so as to reduce the possibility of router bit breakage or bone damage during cutting.

Yet another object of the present invention is to provide an improved surgical router bit which is adapted to cut well at the relatively slow speed of 20,000 rpm.

And another object of the present invention is to provide an improved surgical router bit which minimizes the possibility of burning the bone during cutting.

Another object of the present invention is to provide an improved surgical router bit which uses an improved shearing action to cut the bone.

Still another object of the present invention is to provide an improved surgical router bit which cuts the bone into smaller chips during cutting.

And another object of the present invention is to provide an improved surgical router bit which provides improved evacuation of the severed bone chips during cutting so as to minimize the possibility of clogging the router bit during cutting.

Yet another object of the present invention is to provide an improved surgical router bit which is particularly well adapted to cut the skull.

SUMMARY OF THE INVENTION

These and other objects of the present invention are achieved by a novel surgical router bit which comprises a shaft having a distal end and a proximal end and an outer surface tapering outwardly from its distal end to its proximal end, at least one spiral cutting flute or groove formed in and extending along the length of the shaft from the distal end of the shaft to the proximal end of the shaft, with the at least one spiral cutting flute or groove having a planar floor which is inclined relative to the center axis of the router bit, wherein for each pitch of the at least one spiral cutting flute or groove, the distal end of the floor is level with the tapering outer surface of the shaft and the proximal end of the floor has a fixed depth relative to the tapering outer surface of the shaft so as to define a helical cutting edge of fixed height, and at least one straight cutting flute or groove formed in and extending along the length of the shaft from the distal end of the shaft to the proximal end of the shaft, the at least one straight cutting flute or groove having a fixed depth relative to the tapering outer surface of the shaft so as to define a straight cutting edge of fixed height, and the at least one straight cutting flute or groove being superimposed on and intersecting the at least one spiral cutting flute. Preferably the surgical router bit comprises a plurality of spiral cutting flutes or grooves arcuately spaced apart around the circumference of the shaft, and a plurality of straight cutting flutes or grooves arcuately spaced apart around the circumference of the shaft.

BRIEF DESCRIPTION OF THE DRAWINGS

Still other objects and features of the present invention will be more fully disclosed or rendered obvious in the following detailed description of the invention, which is to be considered together with the accompanying drawings wherein:

FIG. 1 is a side view in elevation showing a conventional surgical router bit of the sort having a plurality of straight cutting flutes;

FIG. 2 is an end view showing the front end of the conventional surgical router bit shown in FIG. 1;

FIG. 3 is a side view in elevation showing a conventional surgical router bit of the sort having a plurality of spiral cutting flutes;

FIG. 4 is an end view showing the front end of the conventional surgical router bit shown in FIG. 3;

FIG. 6 is a side view in elevation showing the new surgical router bit shown in FIG. 5;

FIG. 7 is an end view showing the front end of the new surgical router bit shown in FIGS. 5 and 6;

FIG. 8 is a sectional view taken along line 8—8 of FIG. 6; and

DETAILED DESCRIPTION OF THE INVENTION

Figure 5:
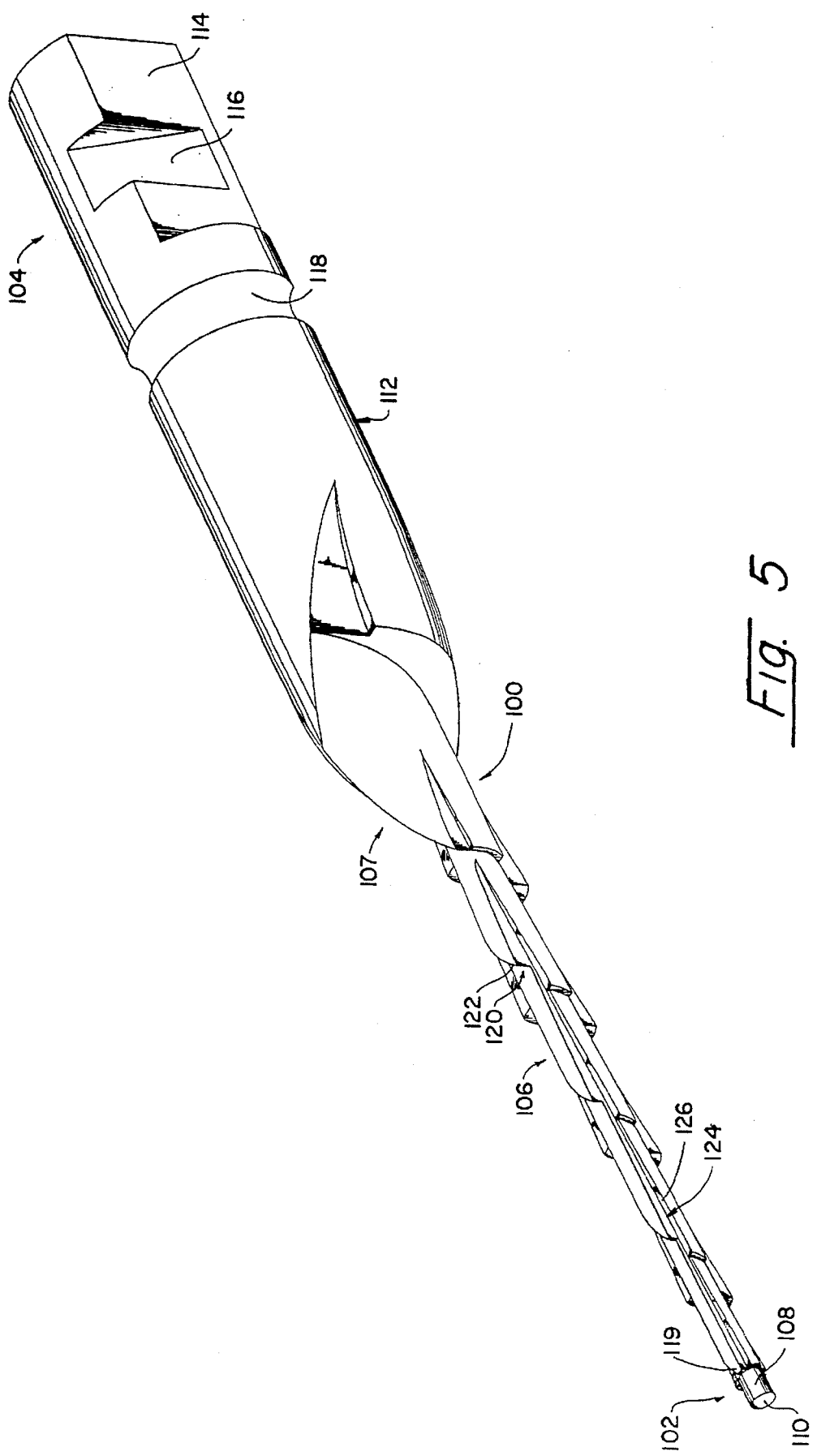
FIG. 5 is a perspective view showing a new surgical router bit made in accordance with the present invention.
Figure 9:
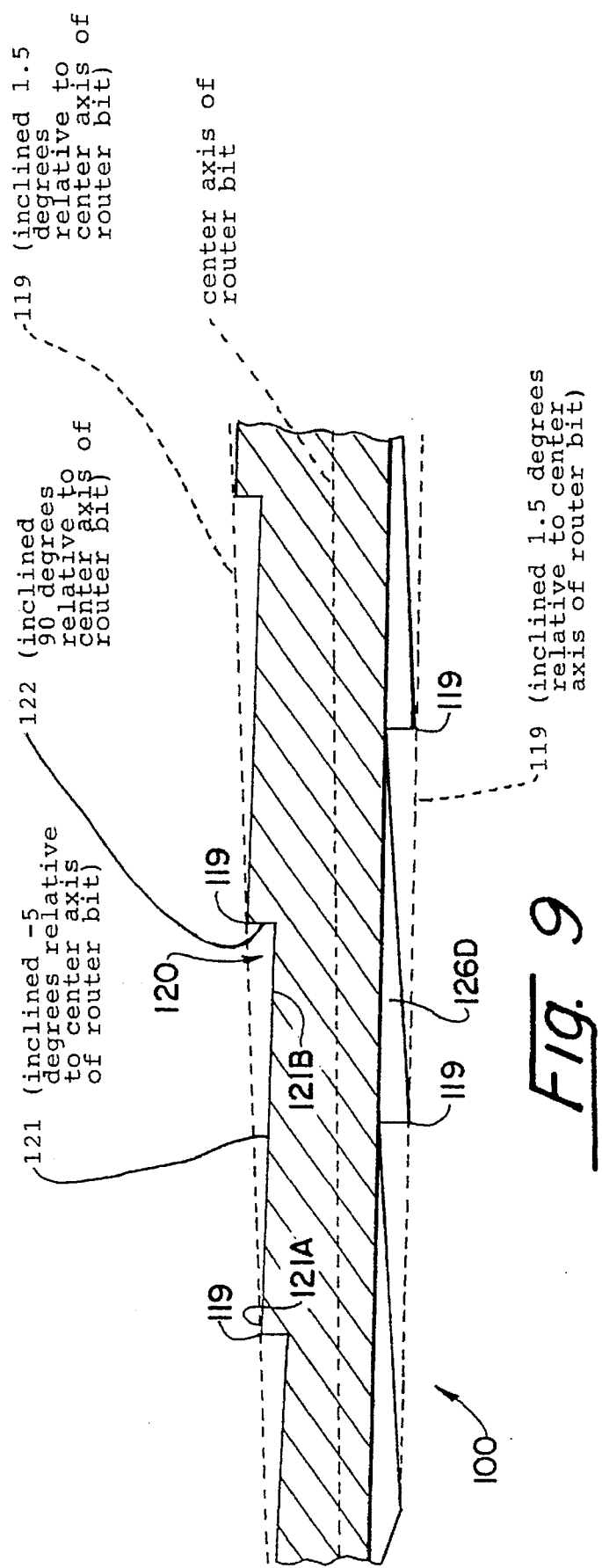
FIG. 9 is a partial sectional schematic view taken along line 9—9 of FIG. 7.

Looking next at FIGS. 5–9, there is shown a surgical router bit 100 formed in accordance with the present invention. Surgical router bit 100 generally comprises a shaft having a distal end 102 and a proximal end 104. An intermediate portion 106 and a transition portion 107 are disposed between distal end 102 and proximal end 104.

Distal end 102 comprises a cylindrical portion 108 terminating in a flat front end surface 110. Cylindrical portion 108 sits closest to the tissue disposed beneath the bone during cutting and serves to terminate the surgical router bit 100 in a relatively blunt front tip for bearing support with associated cutting apparatus (not shown).

Proximal end 104 comprises a generally cylindrical portion 112 which is cut away at 114, notched at 116 and grooved at 118 as shown. Proximal end 104 is adapted to be mounted to a conventional power unit (not shown) in ways well known in the art, i.e., by fitting the generally cylindrical portion 112 into a chuck (also not shown) provided on the conventional power unit and then locking it in place by means (also not shown) provided on the chuck.

Intermediate portion 106 provides the cutting action of the new surgical router bit. The distal end of intermediate portion 106 is attached to cylindrical portion 108 and the proximal end of intermediate portion 106 is attached to transition portion 107. Intermediate portion 106 comprises an outer surface 119 which tapers outwardly at a constant slope from its distal end adjacent cylindrical portion 108 to its proximal end adjacent transition portion 107. Preferably outer surface 119 is inclined at an angle of approximately 1.5 degrees relative to the center axis of the router bit (see FIG. 9). It is to be appreciated that the outer surface 119 of intermediate portion 106 sits above the outer surface of cylindrical portion 108 at the point where intermediate portion 106 adjoins cylindrical portion 108, and the outer surface 119 of intermediate portion 106 sits below the outer surface of generally cylindrical portion 112 at the point where intermediate portion 106 meets transition portion 107. Transition portion 107 joins the rear of intermediate portion 106 to the front of generally cylindrical portion 112.

Intermediate portion 106 also comprises at least one spiral cutting flute or groove 120 formed in and extending along the router bit from the rear of cylindrical portion 108 to the beginning of transition portion 107. Still looking now at FIGS. 5–9, the at least one spiral cutting flute or groove 120 comprises a planar floor 121 which is inclined relative to the center axis of the router bit, wherein for each pitch of the at least one spiral cutting flute or groove 120, the distal end 121A of the floor is level with the tapering outer surface 119 of the shaft and the proximal end 121B of the floor has a fixed depth relative to the tapering outer surface of the shaft so as to define a helical cutting edge 122 of fixed height. Preferably the at least one spiral cutting flute 120 is formed with a pitch of 0.200 inch and floor 121 is inclined at an angle of approximately −5 degrees relative to the center axis of the router bit (and helical cutting edge 122 is inclined at a 90 degree angle relative to the center axis of the router bit), so that helical cutting edge 122 has a fixed height of approximately 0.015 inch. Preferably intermediate portion 106 comprises a plurality of identical spiral cutting flutes 120 arcuately spaced apart around the circumference of the router bit and extending along the router bit from the rear of cylindrical portion 108 to the beginning of transition portion 107, with each of the plurality of spiral cutting flutes 120 defining a helical cutting edge 122. In the case where a plurality of identical spiral cutting flutes 120 are provided, the spiral cutting flutes are preferably equally arcuately spaced apart around the circumference of the router bit; of course, it is also to be appreciated that where a plurality of spiral cutting flutes 120 are provided, the spiral cutting flutes could be unequally arcuately spaced apart around the circumference of the router bit if so desired. Preferably three identical spiral cutting flutes 120A, 120B and 120C (equally arcuately spaced 120 degrees apart around the circumference of the router bit and defining helical cutting edges 122A, 122B and 122C, respectively) are provided, although more or less than that number of spiral cutting flutes may be provided. Each of the spiral cutting flutes 120 is formed with a right hand cut, left hand spiral geometry.

Looking now at FIGS. 5–8, intermediate portion 106 also includes at least one straight cutting flute or groove 124 formed in and extending along the router bit from the rear of cylindrical portion 108 to the front of generally cylindrical portion 112, with the at least one straight cutting flute 124 being superimposed on and intersecting the spiral cutting flutes 120, and the at least one straight cutting flute 124 having a fixed depth relative to the tapering outer surface 119 of intermediate portion 106 so as to define a straight cutting edge 126 of fixed height. Preferably the at least one straight cutting flute 124 is formed so that straight cutting edge 126 has a fixed height of approximately 0.015 inch. Preferably intermediate portion 106 includes a plurality of identical straight cutting flutes 124 arcuately spaced apart around the circumference of the router bit and extending along the router bit from the rear of cylindrical portion 108 to the front of generally cylindrical portion 112. In the case where a plurality of identical straight cutting flutes 124 are provided, the straight cutting flutes are preferably equally arcuately spaced apart around the circumference of the router bit; of course, it is also to be appreciated that where a plurality of straight cutting flutes 124 are provided, the straight cutting flutes could be unequally arcuately spaced apart around the circumference of the router bit if so desired. Preferably four identical straight cutting flutes 124A, 124B, 124C and 124D (equally arcuately spaced 90 degrees apart around the circumference of the router bit and defining straight cutting edges 126A, 126B, 126C and 126D, respectively) are provided, although more or less than that number of straight cutting flutes may be provided. Each of the straight cutting flutes 124 has its straight cutting edge 126 placed along the center line of the router bit and has its base flush with the outer surface of cylindrical portion 108 at the point where the straight cutting flutes meet cylindrical portion 108. Straight cutting flutes 124 are preferably formed by taking a 90 degree section off the center line, although other sections may also be used.

By way of example and not by way of limitation, it has been found that an excellent cranial router bit may be made by forming the cranial router bit with an overall length of approximately 1.750 inches, with cylindrical portion 108 having a length of approximately 0.044 inch and a diameter of approximately 0.040 inch, intermediate portion 106 having a length of approximately 0.750 inch, transition portion 107 having a length of approximately 0.056 inch, and generally cylindrical portion 112 having a length of approximately 0.900 inch and a diameter of approximately 0.156 inch. Intermediate portion 106 is formed from solid stock having an outer surface 119 inclined at approximately 1.5 degrees off the center axis as it extends from cylindrical portion 108 to transition portion 107, with the solid stock having a diameter of 0.070 inch adjacent cylindrical portion 108. Spiral cutting flutes or grooves 120 are formed with a right hand cut, left hand spiral geometry with a pitch of 0.200 inch. Preferably the floors 121 of spiral cutting flutes 120 are inclined at an angle of approximately −5 degrees relative to the center axis of the router bit (and helical cutting edges 122 are inclined at a 90 degree angle relative to the center axis of the router bit), so that the helical cutting edges 122 have a fixed height of approximately 0.015 inch. Three spiral cutting flutes 120 are provided, with the three spiral cutting flutes being equally arcuately spaced apart around the circumference of the router bit. Straight cutting flutes or grooves 124 are formed by taking a 90 degree section off the center line, with the straight cutting flutes having a constant depth of 0.015 inch as measured from the outer surface 119 of the solid stock from which intermediate portion 106 is formed. Four straight cutting flutes 124 are provided, with the four straight cutting flutes 124 being equally arcuately spaced apart around the circumference of the router bit. Each of the straight cutting flutes 124 has its base flush with the outer surface of cylindrical portion 108 at the point where the straight cutting flutes meet cylindrical portion 108.

It is to be appreciated that the new router bit 100 shown in FIGS. 5–9 may also be used to cut bones other than the skull, e.g. the router bit could be used to cut the sternum. Of course, in the situation where router bit 100 is used to cut bones other than the skull, the length of intermediate portion 106 may vary according to the thickness of the bone being cut.

In practice, it has been found that the new surgical router bit 100 shown in FIGS. 5–9 performs far better than either the conventional router bit 2 shown in FIGS. 1 and 2 (i.e., the surgical router bit employing only straight cutting flutes or grooves) or the conventional router bit 8 shown in FIGS. 3 and 4 (i.e., the surgical router bit employing only spiral cutting flutes or grooves). More specifically, the unique geometry of router bit 100 enables the router bit to cut faster, with less clogging of the router bit during cutting, and with less load on the router bit during cutting. The unique geometry of router bit 100 provides an improved shearing action for cutting the bone, and cuts the bone into smaller chips during cutting. In addition, the unique geometry of router bit 100 provides improved evacuation of the severed bone chips during cutting. Furthermore, the unique geometry of router bit 100 enables the router bit to cut very well at the relatively slow speed of 20,000 rpm.

Advantages of the Invention

Numerous advantages are achieved by utilizing the present invention.

For one thing, an improved surgical router bit is provided which avoids the problems associated with prior art surgical router bits.

For another thing, the present invention provides an improved surgical router bit which minimizes clogging of the router bit with bone debris during cutting.

The present invention also provides an improved surgical router bit which minimizes the load on the router bit during cutting, so as to reduce the possibility of router bit breakage or bone damage during cutting.

And the present invention provides an improved surgical router bit which is adapted to cut well at the relatively slow speed of 20,000 rpm.

The present invention also provides an improved surgical router bit which minimizes the possibility of burning the bone during cutting.

And the present invention provides an improved surgical router bit which uses an improved shearing action to cut the bone.

In addition, the present invention provides an improved surgical router bit which cuts the bone into smaller chips during cutting.

And the present invention provides an improved surgical router bit which provides improved evacuation of the severed bone chips during cutting so as to minimize the possibility of clogging the router bit during cutting.

The present invention also provides an improved surgical router bit which is particularly well adapted to cut the skull.

What is claimed is:

1. A surgical router bit comprising:

a shaft comprising a longitudinal axis, a distal end and a proximal end, said distal end of said shaft comprising a first cylindrical portion and said proximal end of said shaft comprising a second cylindrical portion, with said second cylindrical portion having a larger diameter than said first cylindrical portion;

exactly three spiral cutting flutes, each said spiral cutting flute:

(a) having the same direction of rotation, being equally circumferentially spaced from adjacent spiral cutting flutes, and helically extending at a constant positive angle relative to said longitudinal axis so as to radially increase and thereby define a spiral extending from said first cylindrical portion to said second cylindrical portion; and (b) having a floor inclined at a negative angle with respect to said longitudinal axis, said floor including a distal edge and a proximal edge such that for each pitch of said spiral cutting flute, said distal edge of said floor conforms to said spiral and said proximal edge of said floor is located at a fixed depth relative to said distal edge, whereby a radially-extending surface will connect the proximal edge of said floor of one pitch with said distal edge of said floor of an adjacent pitch; and exactly four straight cutting flutes, each said straight cutting flute being formed in and extending along the length of said shaft from said distal end to said proximal end of said shaft, and having a fixed depth relative to said distal edges on said spiral cutting flutes, and each said straight cutting flute comprising a planar surface defining a straight cutting edge, said straight cutting flutes being superimposed on and intermittently intersecting said spiral cutting flutes.

2. A surgical router bit comprising:

an approximately 1.75 inch shaft comprising a longitudinal axis, a distal end, a proximal end, and including an approximately 0.75 inch intermediate portion, said distal end of said shaft comprising an approximately 0.04 inch diameter first cylindrical portion having a first end and a second end, and said proximal end of said shaft comprising a second cylindrical portion with a transition portion being disposed between said intermediate portion and said second cylindrical portion, and further wherein said second cylindrical portion comprises a larger diameter than said first cylindrical portion such that said intermediate portion comprises an approximately 1.5° taper relative to said longitudinal axis;

said intermediate portion comprising exactly three spiral cutting flutes and exactly four straight cutting flutes;

each said spiral cutting flute:

(a) having the same direction of rotation, being equally arcuately spaced-apart around the circumference of said intermediate portion, and helically extending at a constant positive angle relative to said longitudinal axis so as to radially increase at an approximately 0.2 inch pitch and thereby define a spiral extending from said second end of said first cylindrical portion, along the entire length of said intermediate portion and said transition portion, and terminating at said second cylindrical portion; and (b) having a floor inclined at an approximately −5° angle with respect to said longitudinal axis, said floor including a distal edge relative to said longitudinal axis and a proximal edge relative to said longitudinal axis such that for each revolution of said spiral cutting flute about said longitudinal axis, a cutting flight is created wherein said distal edge of said floor conforms to said spiral so as to form a helical cutting edge that is inclined at approximately a 90° angle relative to said longitudinal axis and said proximal edge of said floor is located at a fixed depth relative to said distal edge, whereby a radially-extending surface will connect the proximal edge of said floor of one flight with said distal edge of said floor of an adjacent flight;

and wherein each said straight cutting flute is formed in and extends along the length of said intermediate portion in arcuately-spaced relation one to another about the circumference of said intermediate portion from said second end of said first cylindrical portion to the beginning of said transition portion, and having a fixed depth relative to said distal edges on said spiral cutting flutes of approximately 0.015 inches, and each said straight cutting flute comprising a planar surface defining a straight cutting edge disposed at approximately 90° with respect to said longitudinal axis;

said straight cutting flutes being superimposed on and intermittently intersecting said spiral cutting flutes so as to be capable of yielding very small shavings when said surgical router bit is used to cut bone.

* * * * *